United States Patent [19]

Cholody et al.

[11] Patent Number: 5,231,100
[45] Date of Patent: Jul. 27, 1993

[54] ANTINEOPLASTIC MODIFIED IMIDAZOACRIDINES

[75] Inventors: Wieslaw M. Cholody, Wejherowo; Jerzy K. Konopa, Gdansk, both of Poland

[73] Assignee: British Technology Group Limited, England

[21] Appl. No.: 760,694

[22] Filed: Sep. 16, 1991

[30] Foreign Application Priority Data

Mar. 5, 1991 [GB] United Kingdom ............... 9104548

[51] Int. Cl.$^5$ ............... C07D 471/06; A61K 31/435
[52] U.S. Cl. ................................. 514/288; 546/66
[58] Field of Search ..................... 546/66; 514/288

[56] References Cited

U.S. PATENT DOCUMENTS 5,079,358  1/1992  Sugaya et al. ...................... 546/66

FOREIGN PATENT DOCUMENTS 145226  10/1988  European Pat. Off.
1037377  7/1966  United Kingdom ............... 546/66

OTHER PUBLICATIONS

Cholody et al., J. Med. Chem., 35(2), 378-82, 1992.
Cholody et al., J. Med. Chem., 33(1), 49-52, 1990.
W. M. Cholody et al., J. Med. Chem. 33, 2852-2856 (1990), (No. 10).

Primary Examiner—Marianne M. Cintins
Assistant Examiner—Catherine Scalzo
Attorney, Agent, or Firm—Rosenman & Colin

[57] ABSTRACT

Compounds of formula I:

in which:
R represents: —OH or —OR', wherein R' represents $C_1$–$C_6$ alkyl,
$R_1{}^a$ and $R_1{}^b$, which may be identical or different, represent hydrogen or $C_1$–$C_6$ alkyl, unsubstituted or substituted by a hydroxyl, an amino, a N'-alkylamino or a N',N'-dialkylamino group, such N'-alkyl groups containing 1-4 carbon atoms,
n is 2-5 and
$R_2$ represents hydrogen, or straight chain $C_1$–$C_4$ alkyl, in the form of a free base or a pharmaceutically acceptable acid addition salt are useful in antineoplastic treatment and prophylaxis, especially of leukemias.

14 Claims, No Drawings

ANTINEOPLASTIC MODIFIED IMIDAZOACRIDINES

This invention relates to antineoplastic compounds of particular interest for the treatment of leukemia, to the use thereof, processes for the production of such compounds and intermediates therefor.

Accordingly, the present invention comprises a compound of formula I, optionally in the form of an acid addition salt:

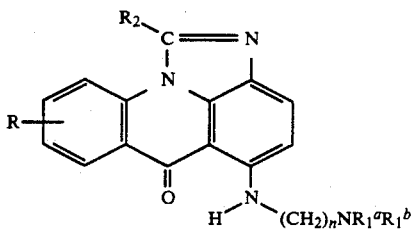

in which

R represents: —OH or —OR' (wherein R' represents alkyl, e.g. $C_1$-$C_6$ alkyl such as methyl).

$R_1{}^a$, and $R_1{}^b$, which may be identical or different, represent hydrogen or alkyl (e.g. $C_1$-$C_3$ alkyl such as methyl) which is optionally substituted e.g. by a hydroxyl, an amino, a N-alkyl-amino or a N,N'-dialkylamino group as, for example in the substituents: hydroxyethyl, aminoethyl, N-alkylaminoethyl and N,N'-dialkylaminoethyl, such N-alkyl groups preferably containing 1-4 carbon atoms.

n is 2-5 and $R_2$ represents hydrogen, or alkyl.

The group R is usually located at the 8-position. $R_1{}^a$ and $R_1{}^b$ are normally identical and represent alkyl groups e.g. $C_1$-$C_6$ alkyl groups such as methyl or ethyl, n typically being 2 or 3.

$R_2$ generally represents hydrogen, straight chain $C_1$-$C_4$ alkyl e.g. methyl or branched chain $C_3$-$C_6$ alkyl.

Addition salts, which are generally pharmaceutically acceptable, may be of both organic and inorganic acids. Examples of suitable acids for salt formation are: hydrochloric, sulfuric, phosphoric, acetic, citric, malonic, ascorbic, maleic, methanesulfonic, lactic, gluconic, glucoronic, and the like. Usually the compound I is present in the form of a hydrochloride and may be hydrated.

The following compounds of formula I are of particular interest:

A. R=9—OH; $R_1{}^a=R_1{}^b=$—$CH_3$; $R_2$=H; n=2.
B. R=8—OH; $R_1{}^a=R_1{}^b=$—$CH_3$; $R_2$=$CH_3$; n=2.
C. R=8—$OCH_3$; $R_1{}^a=R_1{}^b=$—$CH_3$; $R_2$=H; n=2.
D. R=8—OH; $R_1{}^a=R_1{}^b=$—$CH_2CH_3$; $R_2$=H; n=2.
E. R=8—OH; $R_1{}^a=R_1{}^b=$—$CH_2CH_3$; $R_2$=$CH_3$; n=2.
F. R=8—$OCH_3$; $R_1{}^a=R_1{}^b=$—$CH_2CH_3$; $R_2$=H; n=2.
G. R=8—OH; $R_1{}^a=R_1{}^b=$—$CH_3$; $R_2$=$CH_3$; n=3.
H. R=8—OH; $R_1{}^a=R_1{}^b=$—$CH_2CH_3$; $R_2$=H; n=3.

Compounds A, B, E, F and H are of especial interest.

Compounds of formula I in which $R_2$ represents hydrogen or $C_1$-$C_6$ alkyl may be produced by treating a compound of formula II optionally in the form of an acid addition salt thereof,

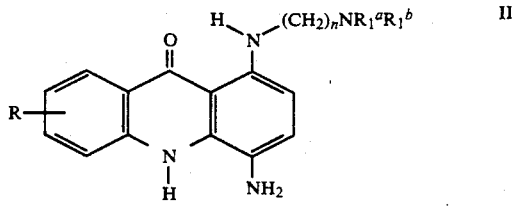

respectively with formic acid or a compound of formula $R_2CON(CH_3)_2$.

Treatment is generally conducted at elevated temperature, typically at reflux.

Compounds of formula II optionally in the form of acid addition salts may be produced from compounds of formula III by treatment thereof to reduce the nitro group to the corresponding amino group:

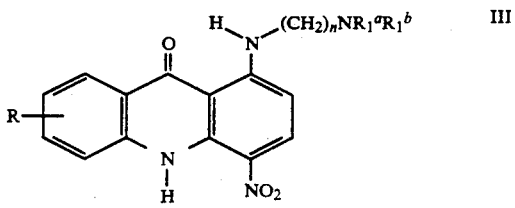

Such treatment may be carried out by means of a reducing agent such as hydrazine hydrate suitably in the presence of a catalyst e.g. Raney Nickel in a polar solvent such as tetrahydrofuran (THF). The intermediates II obtained are generally extremely unstable to oxygen, especially in those compounds wherein n represents 3 and are usually used as starting materials for conversion to compounds of formula I in the form of acid addition salts, for example hydrochlorides.

The present invention further includes within its scope an intermediate of formula II, preferably in the form of an acid addition salt.

Two methods are generally used for isolation of the final products. In the case of methoxy derivatives, the products may be extracted with benzene or chloroform from the reaction mixture after rendering the mixture alkaline and next transformed into dihydrochlorides. The hydroxy compounds may instead be isolated as hydrochloride salts directly from the reaction mixture after acidification with HCl.

Compounds of formula I are of interest for the treatment or prophylaxis of cancers and in particular as antineoplastic agents in the treatment of leukemia.

Accordingly, in a further aspect the present invention comprises a compound of formula I for use in therapy and, in a yet further aspect of the present invention, comprises the use of a compound of formula I for the manufacture of a medicament useful in the treatment or prophylaxis of a cancer and in particular of leukemia.

The dosage form and amount can be readily established by reference to known treatment or prophylactic regimens. In general, however, the dosage of the compound of formula I usually lies within the range about 0.1 mg to about 50 mg/kg, preferably 0.5 mg to 10 mg/kg.

While it is possible for the active compound of formula I or pharmaceutically acceptable salt thereof to be administered alone, it is preferable to present the active compound as a pharmaceutical formulation. Formulations of the present invention for medical use comprise the active compound together with one or more pharmaceutically acceptable carriers therefor, and optionally, any other ingredients which may be therapeutic per se, synergistic with the compound of formula I, or both. Carrier(s) are generally, of course, pharmaceutically acceptable in the sense of being compatible with the other ingredients of the formulation and not deleterious to the recipient thereof.

In accordance with a further aspect, the present invention comprises a pharmaceutical formulation comprising a compound of formula (I) (in the form of the free base or a pharmaceutically acceptable acid addition salt) together with a pharmaceutically acceptable carrier therefor.

Formulations suitable for oral, rectal, topical or parenteral (including subcutaneous, intramuscular and intravenous) administration are included.

Formulations may be conveniently presented in unit dosage form and may be prepared by a methods well known in the art of pharmacy. All methods generally include the step of bringing the active compound into association with a carrier which constitutes one or more accessory ingredients. Usually, the formulations are prepared by uniformly and intimately bringing the active compound into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Tablets may be made by moulding a mixture of the powdered active compound with any suitable carrier in a suitable machine.

A syrup may be made by adding the active compound to a concentrated, aqueous solution of a sugar, for example sucrose, to which may be added an accessory ingredient. Such accessory ingredient(s) may include flavourings, an agent to retard crystallisation of the sugar or an agent to increase the solubility of any other ingredient, such as a polyhydric alcohol, for example glycerol or sorbitol.

Formulations for rectal administration may be presented as a suppository with a usual carrier such as cocoa butter.

Formulations suitable for parenteral administration conveniently comprise a sterile aqueous preparation of the active compound which is preferably isotonic with the blood of the recipient.

In addition to the aforementioned ingredients, formulations of this invention, for example ointments, creams and the like, may include one or more accessory ingredient(s) selected from diluents, buffers, flavouring agents, binders, surface active agents, thickeners, lubricants, preservatives (including antioxidants) and the like.

The present invention is illustrated by the following Examples:

EXAMPLES

General Procedure

Compounds of formula I, the subject of Examples 1 to 16, are produced by the route outlined in Scheme 1.

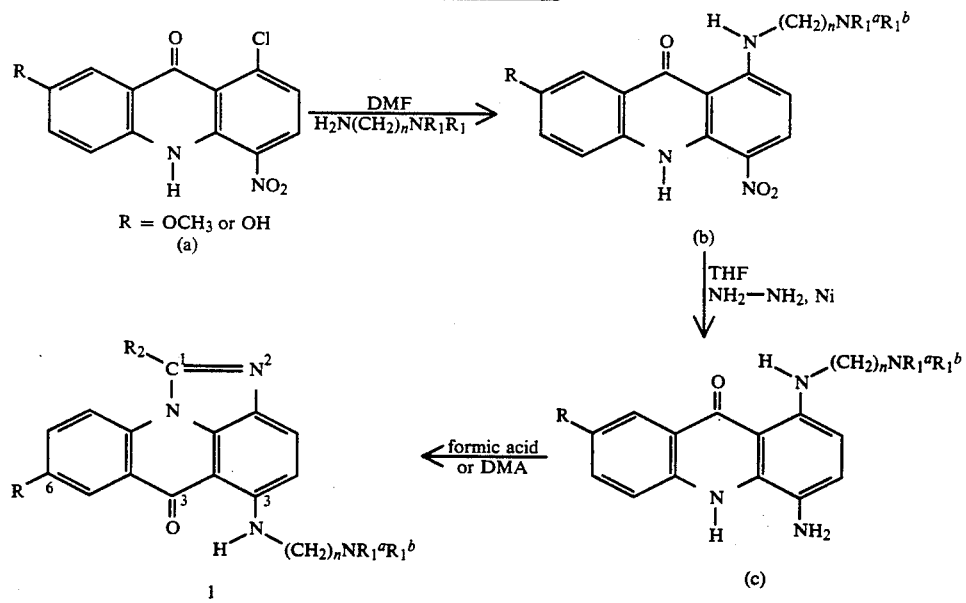

SCHEME 1

In the following Examples melting points are taken on a Bushi 510 capillary melting points apparatus and are uncorrected $^1$H NMR spectra were recorded on a Varian VXR-300 spectrometer operating at 300 MHz. Chemical shifts are reported as δ units in ppm downfield from internal tetramethylsilane. NMR abbreviations used are as follows: br(broad), s(singlet), d(doublet), t(triplet), qu(quartet), qt(quintet), m(multiplet), ex(exchangeable with deuterium oxide). Quartets which by addition of deuterium oxide are transformed into triplets are labeled with *. Single frequency decoupling was utilized to assign specific protons. Coupling constants are given in Hz. Microanalytical results, indicated by atomic symbols, are within ±0.4% of the theoretical values and are obtained from Laboratory of Elemental Analyses, Department of Chemical Sciences, University of Camerino.

EXAMPLE 1

A.
1-[[2-(Diethylamino)ethyl]amino]-7-methoxy-4-nitro-9(1OH)-cridinone

A mixture of 4.57 g (0.015 mol) 1-chloro-7-methoxy-4-nitro-9(1OH)-acridinone, 25 ml DMF and 7.00 g (0.06 mol) 2-diethylaminoethylamine is stirred and heated at 60° C. for 30 minutes. 100 ml 40% (v/v) MeOH-water solution is added to the reaction mixture, heated to boiling and after cooling left overnight in a refrigerator. The crystallized product is collected by filtration washed with water (150 ml) and MeOH (50 ml) and dried to give 5.30 g. (92%) analytically pure product as yellow needles: mp 178°–179° C. (lit. mp. Capps. D. B. European Patent Appl. E.P. 145226, 1985; Chem. Abstr. 1985, 103, 215182s. 179°–180° C.);

B. Preparation of 7-Substituted 4-amino-1-[[(dialkylamino)alkyl]amino]-4-nitro-9(1OH)-acridinone Hydrochloride Salts To a mixture of nitro derivatives (0.01 mol), 200 ml THF, and about 2.5 g of Raney Ni is added with stirring at room temperature then 2 ml hydrazine monohydrate, and stirring if continued for about 30 minutes. The catalyst is filtered off and washed with THF (50 ml). The filtrate is quickly treated with 10 ml concentrated hydrochloric acid and stirred for 10 minutes. The yellow precipitate obtained is collected and washed with THF. The product is recrystallized from a solution of MeOH (90%)-dioxane made acidic with HCl (pH~2).

C. Preparation of 5-[[2-(Diethylamino)ethyl]amino]-8-methoxyimidazo[4,5,1-de] acridin-6-one Dihydrochloride A mixture of 1.71 g (4 mmol) of the product from the procedure of Example 1B and 20 ml (95% formic acid is heated at reflux for 6 h. Acid is evaporated and the residue is dissolved in water (100 ml). The solution is made basic (pH 9) by addition of sodium carbonate and product is extracted with chloroform (2×100 ml). The organic extracts are dried and evaporated to give a residue which is dissolved in EtOH. The solution is made acidic with HCl and product is crystallized by addition of acetone to give the title product.

EXAMPLE 2

Compound I: n=2, R=OCH$_3$, R$_1$=CH$_3$, R$_2$=H.

The procedures 1A, 1B and 1C of Example 1 are followed but dimethylaminoethylamine is used in place of diethylaminoethylamine in 1A.

EXAMPLE 3

Compound I: n=2, R=OCH$_3$, R$_1$=CH$_3$, R$_2$=CH$_3$.

The procedures 1A and 1B of Example 1 are followed using dimethylaminoethylamine in place of diethylaminoethylamine. The product is then subjected to the following procedure (designated 3C):

A mixture of 2.14 g (5 mmol) hydrochloride and 30 ml DMA is refluxed for 12 h, 200 ml water is added to the reaction mixture, made basic with sodium hydroxide and the product is extracted with benzene (2.150 ml). The extracts are evaporated to dryness and the residue is dissolved in methanol-dioxane (1:1) mixture. The solution is made acidic with gaseous HCl and the crystallized product is collected by filtration to give yellow crystals.

EXAMPLE 4

Compound I: n=2, R=OCH$_3$, R$_1$=CH$_2$CH$_3$, R$_2$=CH$_3$.

The procedures 1A and 1B of Example 1 are followed and the product is subjected to procedure 3C.

EXAMPLE 5

Compound I: n=3, R=OCH$_3$, R$_1$=CH$_3$, R$_2$=H.

The procedures 1A, 1B and 1C of Example 1 are followed but dimethylaminopropylamine is used in place of diethylaminoethylamine in procedure 1A.

EXAMPLE 6

Compound I: n=3, R=OCH$_3$, R$_1$=CH$_3$, R$_2$=CH$_3$.

The procedure of Example 5 is followed but procedure 3C replaced procedure 1C.

EXAMPLE 7

Compound I: n=3, R=OCH$_3$, R$_1$=CH$_2$CH$_3$, R$_2$=H.

The procedures 1A, 1B and 1C of Example 1 are followed but diethylaminopropylamine is used in place of diethylaminoethylamine in procedure 1A.

EXAMPLE 8

Compound I: n=3, R=OCH$_3$, R$_1$=CH$_2$CH$_3$, R$_2$=CH$_3$.

The procedure of Example 7 is followed but procedure 3C replaces procedure 1C.

EXAMPLE 9

Compound I: n=2, R=OH, R$_1$=CH$_3$, R$_2$=H.

The procedure of Example 1 is followed but dimethylaminoethylamine is used in place of diethylaminoethylamine and 1-chloro-7-hydroxy-4-nitro-9(1OH)-acridone is used in place of 1-chloro-7-methoxy-4-nitro-9-(1OH)-acridone in procedure 1A and procedure 1C is replaced by the following, designated 9C:

A mixture of 5 mmol of dihydrochloride salt and 20 ml of 95% formic acid is refluxed for 8 h. Formic acid is evaporated and the residue is dissolved on heating in methanol. 3 ml conc. hydrochloric acid is added to the hot solution and the product is crystallized by addition of acetone. The product is collected by filtration and recrystallized from a methanol-acetone mixture.

EXAMPLE 10

Compound I: n=2, R=OH, R$_1$=CH$_3$, R$_2$=CH$_3$.

The procedure of Example 9 is followed but the following procedure, designated 10C, replaces 9C:

A mixture of 5 mmol of dihydrochloride salt and 25 ml of DMA is refluxed for 12 h. About 20 ml of the solvent is evaporated, 100 ml acetone is added to the residue and acidified with gaseous HCl. The precipitated product is collected by filtration and washed with acetone. Crude product is recrystallized (if necessary twice) from methanol-acetone to give the respective dihydrochloride salt.

EXAMPLE 11

Compound I: n=2, R=OH, R$_1$=CH$_2$CH$_3$, R$_2$=H.

The procedure of Example 9 is followed but diethylaminoethylamine is used in place of dimethylaminoethylamine in procedure 1A.

EXAMPLE 12

Compound I: n=2, R=OH, R$_1$=CH$_2$CH$_3$, R$_2$=CH$_3$.

The procedure of Example 10 is followed but diethylaminoethylamine is used in place of dimethylaminoethylamine in procedure 1A.

EXAMPLE 13

Compound I: n=3, R=OH, R$_1$=CH$_3$, R$_2$=H.

The procedure of Example 9 is followed but dimethylaminopropylamine is used in place of dimethylaminoethylamine in procedure 1A.

EXAMPLE 14

Compound I: n=3, R=OH, R$_1$=CH$_3$, R$_2$=CH$_3$.

The procedure of Example 13 is followed but procedure 10C replaces procedure 9C.

EXAMPLE 15

Compound I: n=3, R=OH, R$_1$=CH$_2$CH$_3$, R$_2$=H.

The procedure of Example 13 is followed but diethylaminopropylamine is used in place of dimethylaminopropylamine in procedure 1A.

EXAMPLE 16

Compound I: n=3, R=OH, R$_1$=CH$_2$CH$_3$, R$_2$=CH$_3$.

The procedure of Example 15 is followed but procedure 10C replaces procedure 9C.

NMR data for intermediates and final products follows with reference to Scheme 1:

Compound (b): R=OCH$_3$, R$_1$=CH$_2$CH$_3$, n=2.

$^1$H NMR (Me$_2$CO-d$_6$) δ 12.48(s,1H,ex,N10-H), 11.90(t,1H,ex,—NH—CH$_2$—), 8.34(d,1H,J=9.8,C3-H), 7.93(d,1H,J=9.0,C5-H), 7.56(d,1H,J=3.0,C8-H), 7.40(dd,1H,J=8.9,J=3.0,C6-H), 6.54(d,1H,J=9.8,C2-H), 3.87(s,3H,—OCH$_3$), 3.49(qu*,2H,—NH—CH$_2$—CH$_2$—), 2.73(t,2H,—CH$_2$—CH$_2$—NEt$_2$), 2.58(qu,4H,—N(CH$_2$CH$_3$)$_2$), 1.02(t,6H,—N(CH$_2$—CH$_3$)$_2$).

Compound (b): R=OH, R$_1$=CH$_2$CH$_3$, n=2.

$^1$H NMR (Me$_2$SO-d$_6$) δ 12.40(s,1H,ex, N10-H), 11.92(t,1H,ex,—NH—CH$_2$—), 9.74(s,1H,ex,—OH), 8.34(d,1H,J=9.8,C3-H), 7.79(d,1H,J=8.9,C5-H), 7.55(d,1H,J=2.8,C8-H), 7.26(dd,1H,J=8.9,J=2.8,C6-H), 6.53(d,1H,J=10.0,C2-H), 3.49(qu*,2H,—NH—CH$_2$,—CH$_2$—), 2.74(t,2H,—CH$_2$—CH$_2$—NEt$_2$), 2.58(qu,4H,—N(CH$_2$—CH$_3$)$_2$), 1.02(t,6H,—N(CH$_2$—CH$_3$)$_2$).

Compound (c): R=OCH$_3$, R$_1$=CH$_2$CH$_3$, n=3.

$^1$H NMR (Me$_2$SO-d$_6$+D$_2$O) δ 7.80(d,1H,J=9.0,C5-H), 7.58(d,1H,J=3.0,C8-H), 7.55(d,1H,J=8.8, C3-H), 7.43(dd,1H,J=9.0,J=3.0,-C6-H), 6.35(d,1H,J=8.8,C2-H), 3.85(s,3H,—OCH$_3$), 3.35(t,2H,—NH—CH$_2$—CH$_2$—), 3.12(m,6H,—CH$_2$—N(CH$_2$—CH$_3$)$_2$), 2.07(m,2H,—CH$_2$—CH$_2$—CH$_2$—), 1.23(t,6H,—N(CH$_2$CH$_3$)$_2$).

Compound I: R=OCH$_3$, R$_1$=CH$_2$CH$_3$, R$_2$=H, n=2.

$^1$H NMR (free base)(Me$_2$SO-d$_6$) δ 9.13(s,1H,C1-H), 8.98(t,1H,ex,—NH—CH$_2$—), 8.36(d,1H,J=9.1,C10-H), 7.98(d,1H,J=8.9,C3-H), 7.79(d,1H,J=3.0,C7-H), 7.52(dd,1H,J=9.1,J=3.0,C9-H), 6.80(d,1H,J=8.9,C4-H), 3.92(s,3H,—OCH$_3$), 3.42(qu*,2H,—NH—CH$_2$—CH$_2$—), 2.73(t,2H,—CH$_2$—CH$_2$—NEt$_2$), 2.58(qu,4H,—N(CH$_2$—CH$_3$)$_2$), 1.02(t,6H,—N(CH$_2$—CH$_3$)$_2$).

Compound I: R=OCH$_3$, R$_1$=CH$_2$CH$_3$, R$_2$=CH$_3$, n=2.

$^1$H, NMR (free base) (Me$_2$SO-d$_6$) δ 8.98(t,1H,ex,—NH—CH$_2$), 8.12(d,1H,J=9.2,C10-H), 7.82(d,1H,J=3.2,C7-H), 7.80(d,1H,J=8.8,C3-H), 7.43(dd,1H,J=9.2,J=3.2,C9-H), 6.70(d,1H,J=8.8,C4-H), 3.91(s,3H,—OCH$_3$), 3.38(qu*,2H,—NH—CH$_2$—CH$_2$—), 3.00(s,3H,Cl—CH$_3$), 2.72(t,2H,—CH$_2$—CH$_2$—NEt$_2$), 2.58(qu,4H,—N(CH$_2$—CH$_3$)$_2$), 1.03(t,6H,—N(CH$_2$—CH$_3$)$_2$).

Compound I: R=OH, R$_1$=CH$_2$CH$_3$, R$_2$=H, n=2.

$^1$H NMR (free base) (Me$_2$SO-d$_6$) δ 10.00(s,1H,ex,C8-OH), 9.08(s,1H,C1-H), 8.99(t,1H,ex,—NH—CH$_2$—), 8.26(d,1H,J=8.9,C10-H), 7.95(d,1H,J=8.8,C3-H), 7.72(d,1H,J=2.8,C7-H), 7.33(dd,1H,J=8.9,J=2.8,C9-H), 6.77(d,1H,J=8.8,C4-H), 3.40(qu*,2H,—NH—CH$_2$—CH$_2$—), 2.70(t,2H,—CH$_2$—CH$_2$—NEt$_2$), 2.56(qu,4H,—N(CH$_2$—CH$_3$)$_2$), 1.01(t,6H,—N(CH$_2$—CH$_3$)$_2$).

Compounds I: R=OH, R$_1$=CH$_2$CH$_3$, R$_2$=H, n=3.

$^1$H NMR (free base) (ME$_2$SO-d$_6$) δ 10.02(brs,1H,ex,C8-OH), 9.10(s,1H,C1-H), 8.93(t,1H,ex,—NH—CH$_2$—), 8.27(d,1H,J=8.9,C10-H), 7.97(d,1H,J=8.8,C3-H), 7.73(d,1H,J=2.8,C7-H), 7.34(dd,1H,J=8.9,J=2.8,C9-H), 6.81(d,1H,J=8.8,C4-H), 3.42(qu*,2H,—NH—CH$_2$—CH$_2$—), 2.52(t,2H,—CH$_2$—CH$_2$—NEt$_2$), 2.48(qu,4H,—N(CH$_2$,CH$_3$)$_2$), 1.78(qt,2H,—CH$_2$—CH$_2$—CH$_2$—), 0.96(t,6H,—N(CH$_2$—CH$_3$)$_2$).

Compound 1: R=OH, R$_1$=CH$_3$, R$_2$=H, n=2.

$^1$H NMR (free base) (ME$_2$SO-d$_6$) δ 10.00(s,1H,ex,C8-OH), 9.02(t,1H,ex,—NH—CH$_2$—), 8.11(d,1H,J=9.1,C10-H), 7.83(d,1H,J=8.8,C3-H), 7.79(d,1H,J=2.9,C7-H), 7.33(dd,1H,J=9.1,J=2.9,C9-H), 6.72(d,1H,J=8.8,C4-H), 3.38(qu*,2H,—NH—CH$_2$—CH$_2$—), 3.02(s,3H,Cl—CH$_3$), 2.72(t,2H,—CH$_2$—CH$_2$—NEt$_2$), 2.56(qu,4H,—N(CH$_2$—CH$_3$)$_2$), 1.02(t,6H,—N(CH$_2$—CH$_3$)$_2$).

Compound I: R=OH, R$_1$=CH$_2$CH$_3$, R$_2$=CH$_3$, n=3.

$^1$H NMR (free base) (Me$_2$SO-d$_6$) δ 10.0(br s,1H,ex,C8-OH), 8.91(t,1H,ex,—NH—CH$_2$—), 8.08(d,1H,J=9.1,C10-H), 7.80(d,1H,J=8.8,C3-H), 7.77(d,1H,J=3.0,C7-H), 7.32(dd,1H,J=9.1,J=3.0,C9-H), 6.70(d,1H,J=8.8,C4-H), 3.38(qu*,2H,—NH—CH$_2$—CH$_2$—), 3.00(s,3H,Cl—CH$_3$), 2.48(m,6H,—CH$_2$—CH$_2$—N(CH$_2$—CH$_3$)$_2$), 1.76(qt,2H,—CH$_2$—CH$_2$—CH$_2$—).

Intermediates

Melting points, yields and molecular formulae of intermediates are set forth in Table I with reference to Scheme 1.

TABLE I

1-Substituted 4-Nitro-9(10H)-acridinones (b) and
1-Substituted 4-Amino-7-methoxy-9-(10H)-acridinones (c)

| Compd | n | R | R$_1$ | mp, °C. | yield, % | molecular formula[a] |
|---|---|---|---|---|---|---|
| (b) | 2 | OCH$_3$ | CH$_3$ | 242–243[b] | 96 | C$_{18}$H$_{20}$N$_4$O$_4$ |
| (b) | 2 | OCH$_3$ | CH$_2$CH$_3$ | 178–179[c] | 92 | C$_{20}$H$_{24}$N$_4$O$_4$ |
| (b) | 3 | OCH$_3$ | CH$_3$ | 165–166 | 94 | C$_{19}$H$_{22}$N$_4$O$_4$ |
| (b) | 3 | OCH$_3$ | CH$_2$CH$_3$ | 153–154[d] | 97 | C$_{21}$H$_{26}$N$_4$O$_4$ |
| (b) | 2 | OH | CH$_3$ | 258–260 | 90 | C$_{17}$H$_{18}$N$_4$O$_4$ |
| (b) | 2 | OH | CH$_2$CH$_3$ | 227–229 | 94 | C$_{19}$H$_{22}$N$_4$O$_4$ |

TABLE I-continued

1-Substituted 4-Nitro-9(10H)-acridinones (b) and
1-Substituted 4-Amino-7-methoxy-9-(10H)-acridinones (c)

| Compd | n | R | $R_1$ | mp, °C. | yield, % | molecular formula[a] |
|---|---|---|---|---|---|---|
| (b) | 3 | OH | $CH_3$ | 214–214[e] | 82 | $C_{18}H_{20}N_4O_4$ |
| (b) | 3 | OH | $CH_2CH_3$ | 208–210 | 86 | $C_{20}H_{24}N_4O_4$ |
| (c) | 2 | $OCH_3$ | $CH_3$ | 240–243 dec | 79 | $C_{18}H_{22}N_4O_2$, 2HCl |
| (c) | 2 | $OCH_3$ | $CH_2CH_3$ | 227–231 dec | 74 | $C_{20}H_{26}N_4O_2$, 2HCl |
| (c) | 3 | $OCH_3$ | $CH_3$ | 232–235 dec | 80 | $C_{19}H_{24}N_4O_2$, 2HCl |
| (c) | 3 | $OCH_3$ | $CH_2CH_3$ | 180–185 dec | 84 | $C_{21}H_{28}N_4O_2$, 3HCl |

[a]The analyses are within ±0.4% of the theoretical values for C, H and N. [lit[b]mp 234–237° C.; [c]mp 179–180° C.; [d]mp 151–152° C.; [e]mp 212–213° C.; (Capps, D. B. European Patent Appl. EP 145226, 1985; Chem. Abstr. 1985, 103, 215182s)].

Biological Tests

In Vitro Cytoxicity Evaluation

The mouse L1210 leukemia cells (RPM1, USA) are grown in RPM1 1640 medium supplemented with 5% fetal calf serum and penicillin (1,000,000 units litre) plus streptomycin (100 mg/litre) in controlled air-5% $CO_2$ humidified atmosphere at 37° C. L1210 mouse leukemia cells are seeded at a density of $5.10^4$ cells/ml. The tested compounds after being dissolved in 50% ethanol are added, at four different concentrations, to the cell suspensions. The cytotoxic activity ($IC_{50}$ value) of the tested compounds is defined as their concentrations causing 50% growth inhibition after 48 h, measured by cells protein contents and is determined from dose-response curves by the method of: Konopa, J.; Matuszkiewicz, A.; Hrabowska, M.; Onoszko, K. Arzneim.-Forsch. 1974, 24, 1971.

In Vivo Antileukemic Evaluation $BDF_1$ mice are injected ip with $10^6$ P388 lymphotic leukemia cells on day O and treated ip on days 1–5 in accordance with the protocols described by the National Cancer Institute: Geran, R. I.; Greenberg, R. H.; MacDonald, M. M.; Schumacher, A. M.; Abbot, B. J. Cancer Chemother, Re., Part 3, 1972,3,1. The mean survival time (MST) for each treatment group (eight mice) is calculated and the percent of T/C was determined by using the following formula: % T/C=(MST treated)/(MST control) 100.

Results of the Cytotoxicity Evaluation and Antileukemic Evaluation are set forth in Table II:

TABLE II

Formulae, melting paint, yields and activities against Murine L1210 in Vitro and P388 Leukemia in Vivo of Substituted 5-Aminoimidazo[4,5,1-de]acridin-6-ones of formula I

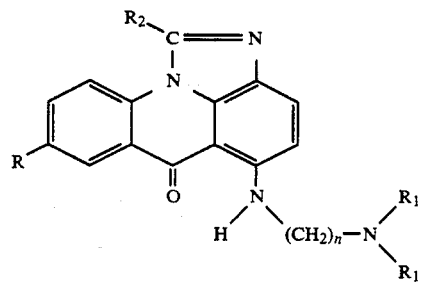

| Example | n | R | $R_1$ | $R_2$ | mp. °C.[a] | yield % | formula[b] | in vitro $IC_{50}$ (μg/ml) | (μM) | P388 leukemia in vivo opt dose (mg/kg/ per inj) | % TC[c] |
|---|---|---|---|---|---|---|---|---|---|---|---|
| 1 | 2 | $OCH_3$ | $CH_2CH_3$ | H | 250–254 dec[d] | 68 | $C_{21}H_{24}N_4O_2$ 1.75HCl | 0.78 (±0.02) | 1.8 | 100 | 183, 209 |
| 2 | 2 | $OCH_3$ | $CH_3$ | H | 254–258 dec | 90 | $C_{19}H_{20}N_4O_2$ 1.5HCl 0.75H$_2$O | 0.65 (±0.07) | 1.6 | 100 | 177, 136 |
| 3 | 2 | $OCH_3$ | $CH_3$ | $CH_3$ | 255–259 dec | 82 | $C_{20}H_{22}N_4O_2$ 2 HCl.H$_2$O | 0.34 (±0.09) | 0.77 | 150 | 127 |
| 4 | 2 | $OCH_3$ | $CH_2CH_3$ | $CH_3$ | 238–241 dec[e] | 70 | $C_{22}H_{28}N_4O_2.2$ HCl | 0.70 (±0.40) | 1.55 | 150 | 136, 120 |
| 5 | 3 | $OCH_3$ | $CH_3$ | H | 237–241 dec | 70 | $C_{20}H_{22}N_4O_2.2$ HCl.0.2H$_2$O | 3.50 (±0.75) | 8.25 | 150 | 164 |
| 6 | 3 | $OCH_3$ | $CH_3$ | $CH_3$ | 252–256 dec[f] | 68 | $C_{21}H_{24}N_4O_2.1.85$ HCl | 1.40 (±0.60) | 3.2 | 150 | 136 |
| 7 | 3 | $OCH_3$ | $CH_2CH_3$ | H | 246–250 dec | 72 | $C_{22}H_{26}N_4O_2.1.5$ HCl | 1.10 (±0.32) | 2.5 | 150 | 142 |
| 8 | 3 | $OCH_3$ | $CH_2CH_3$ | $CH_3$ | 203–208 dec | 64 | $C_{23}H_{28}N_4O_2.2$ HCl.H$_2$O | 0.70 (±0.17) | 1.4 | 150 | 108 |
| 9 | 2 | OH | $CH_3$ | H | 260–264 dec | 77 | $C_{18}H_{18}N_4O_2.2$ HCl.H$_2$O | 0.02 (±0.01) | 0.048 | 12.5 | 210, 210 |
| 10 | 2 | OH | $CH_3$ | $CH_3$ | 268–273 dec | 68 | $C_{19}H_{20}N_4O_2.2$ HCl.2H$_2$O | 0.06 (±0.03) | 0.135 | 12.5 | 200, 250 |
| 11 | 2 | OH | $CH_2CH_3$ | H | 250–255 dec[g] | 72 | $C_{20}H_{22}N_4O_2.2$ HCl.H$_2$O | 0.013 (±0.008) | 0.031 | 5 | 211, 175 |
| 12 | 2 | OH | $CH_2CH_3$ | $CH_3$ | 260–265 dec[h] | 78 | $C_{21}H_{24}N_4O_2.1.5$HCl 0.5H$_2$O | 0.11 (±0.08) | 0.25 | 75 | 280, 290 |
| 13 | 3 | OH | $CH_3$ | H | 247–251 dec | 70 | $C_{19}H_{20}N_4O_2.2$ HCl | 0.014 (±0.005) | 0.034 | 5 | 183 |
| 14 | 3 | OH | $CH_3$ | $CH_3$ | 268–271 dec[i] | 69 | $C_{20}H_{22}N_4O_2.2$ HCl.0.5H$_2$O | 0.10 (±0.07) | 0.23 | 100 | 255 |
| 15 | 3 | OH | $CH_2CH_3$ | H | 269–272 dec[j] | 70 | $C_{21}H_{21}N_4O_2.2$ HCl.H$_2$O | 0.08 (±0.05) | 0.18 | 25 | 309, 230 |
| 16 | 3 | OH | $CH_2CH_3$ | $CH_3$ | 238–242 dec[k] | 66 | $C_{22}H_{26}N_4O_2.2$ HCl.H$_2$O | 0.40 (±0.21) | 0.89 | 25 | 150, |

TABLE II-continued

Formulae, melting paint, yields and activities against Murine L1210 in Vitro and P388 Leukemia in Vivo of Substituted 5-Aminoimidazo[4,5,1-de]acridin-6-ones of formula I

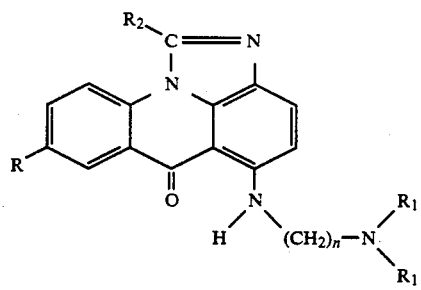

| Example | n | R | $R_1$ | $R_2$ | mp, °C.[a] | yield % | formula[b] | in vitro $IC_{50}$ (μg/ml) | (μM) | P388 leukemia in vivo opt dose (mg/kg/ per inj) | % TC[c] |
|---|---|---|---|---|---|---|---|---|---|---|---|
| | | | | | | | | | | | 155 |

[*] All the hydrochlorides were recrystallized from MeOH-acetone and free bases from benzene-hexane.
[b] Microanalyses are within ±0.4% of the theoretical values for C, H and N.
[c] When two values are given, the second one represents the result obtained during repeated independent multidose assay.
[d] Free base mp 191–193° C.
[e] Free base mp 156–158° C.
[f] Free base mp 156–158° C.
[g] Free base mp 239–242° C.
[h] Free base mp 255–258° C.
[i] Free base mp 242–245° C.
[j] Free base mp 222–225° C.
[k] Free base mp 240–245° C.

We claim:

1. Compounds of formula I:

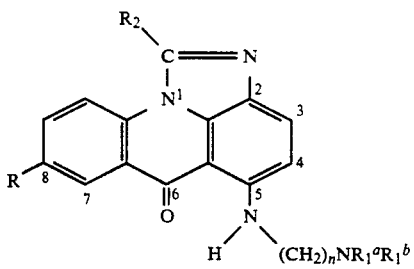

in which:

R represents: —OH or —OR', wherein R' represents $C_1$–$C_6$ alkyl, $R_1{}^a$ and $R_1{}^b$, which may be identical or different, represent hydrogen or $C_1$–$C_6$ alkyl, unsubstituted or substituted by a hydroxyl, an amino, a N'-alkylamino or a N',N'-dialkylamino group, such N'-alkyl group containing 1–4 carbon atoms, n is 2–5 and $R_2$ represents hydrogen, or straight chain $C_1$–$C_4$ alkyl, in the form of a free base or a pharmaceutically acceptable acid addition salt thereof.

2. Compounds according to claim 1, in which $R_1{}^a$ and $R_1{}^b$ are identical.

3. Compounds according to claim 1, in which $R_1{}^a$ and $R_1{}^b$ or both represent a said substituted or unsubstituted $C_1$–$C_3$ alkyl group.

4. Compounds according to claim 1, in which n is 2 or 3.

5. Compounds according to claim 1, in which R=—OH, $R_1{}^a$=$R_1{}^b$=methyl or ethyl, $R_2$=hydrogen or methyl and n is 2 or 3.

6. The compound according to claim 1 wherein: R=—OH; $R_1{}^a$=$R_1{}^b$=—$CH_3$; $R_2$=H; and n=2.

7. The compound according to claim 1 wherein: R=—OH; $R_1{}^a$=$R_1{}^b$=—$CH_3$; $R_2$=$CH_3$; and n=2.

8. The compound according to claim 1 wherein: R=—$OCH_3$; $R_1{}^a$=$R_1{}^b$=—$CH_3$; $R_2$=H; and n=2.

9. The compound according to claim 1 wherein: R=—OH; $R_1{}^a$=$R_1{}^b$=—$CH_2CH_3$; $R_2$=H; and n=2.

10. The compound according to claim 1 wherein: R=—OH; $R_1{}^a$=$R_1{}^b$=—$CH_2CH_3$; $R_2$=$CH_3$; and n=2.

11. The compound according to claim 1 wherein: R=—$OCH_3$; $R_1{}^a$=$R_1{}^b$=—$CH_2CH_3$; $R_2$=H; and n=2.

12. The compound according to claim 1 wherein: R=—OH; $R_1{}^a$=$R_1{}^b$=—$CH_3$; $R_2$=$CH_3$; and n=2.

13. The compound according to claim 1 wherein: R=—OH; $R_1{}^a$=$R_1{}^b$=—$CH_2CH_3$; $R_2$=H; and n=2.

14. A method for prophylaxis of leukemia which comprises administering to a patient an effective amount of an antineoplastic compound of formula (I) according to claim 1.

* * * * *